United States Patent
Mukunda et al.

(10) Patent No.: US 10,751,300 B2
(45) Date of Patent: Aug. 25, 2020

(54) COMPOSITION AND METHOD FOR TREATING SEIZURE DISORDERS

(71) Applicant: India Globalization Capital, Inc., Bethesda, MD (US)

(72) Inventors: Ramachandra Mukunda, Potomac, MD (US); Ranga Chelva Krishna, Englewood, NJ (US)

(73) Assignee: India Globalization Capital, Inc., Potomac, MD (US)

( * ) Notice: Subject to any disclaimer, the term of this patent is extended or adjusted under 35 U.S.C. 154(b) by 0 days.

(21) Appl. No.: 15/104,556

(22) PCT Filed: Jan. 14, 2016

(86) PCT No.: PCT/US2016/013323
§ 371 (c)(1),
(2) Date: Jun. 15, 2016

(87) PCT Pub. No.: WO2016/118391
PCT Pub. Date: Jul. 28, 2016

(65) Prior Publication Data
US 2018/0161285 A1  Jun. 14, 2018

Related U.S. Application Data

(60) Provisional application No. 62/107,432, filed on Jan. 25, 2015.

(51) Int. Cl.
| | | |
|---|---|---|
| *A61K 31/07* | (2006.01) | |
| *A61K 31/515* | (2006.01) | |
| *A61K 45/06* | (2006.01) | |
| *A61K 36/185* | (2006.01) | |
| *A61P 25/08* | (2006.01) | |
| *A61K 31/513* | (2006.01) | |
| *A61K 31/05* | (2006.01) | |

(52) U.S. Cl.
CPC .............. *A61K 31/07* (2013.01); *A61K 31/05* (2013.01); *A61K 31/513* (2013.01); *A61K 31/515* (2013.01); *A61K 36/185* (2013.01); *A61K 45/06* (2013.01); *A61P 25/08* (2018.01); *A61K 2300/00* (2013.01)

(58) Field of Classification Search
USPC ........................................................ 514/576
See application file for complete search history.

(56) References Cited

U.S. PATENT DOCUMENTS

| | | |
|---|---|---|
| 5,240,937 A | 8/1993 | Kelley |
| 5,391,740 A | 2/1995 | Wang et al. |
| 6,683,086 B2 | 1/2004 | Druzgala et al. |
| 6,949,582 B1 | 9/2005 | Wallace |
| 8,859,540 B2 | 10/2014 | Rundfeldt et al. |
| 2004/0043043 A1 | 3/2004 | Schlyter et al. |
| 2004/0138293 A1 | 7/2004 | Werner et al. |
| 2005/0042172 A1 | 2/2005 | Whittle |
| 2006/0127499 A1 | 6/2006 | Lazarev et al. |
| 2006/0257502 A1 | 11/2006 | Liu |
| 2007/0293440 A1 | 12/2007 | Smith-Swintosky et al. |
| 2007/0293476 A1 | 12/2007 | Smith-Swintosky et al. |
| 2008/0254017 A1 | 10/2008 | Kane et al. |
| 2010/0035978 A1 | 2/2010 | Guy et al. |
| 2011/0217278 A1 | 9/2011 | Felder |
| 2011/0301238 A1 | 12/2011 | Borges |
| 2012/0004251 A1 | 1/2012 | Whalley et al. |
| 2012/0165402 A1 | 6/2012 | Whalley et al. |
| 2012/0322782 A1 | 12/2012 | Narishetty et al. |
| 2013/0065898 A1 | 3/2013 | Rundfeldt et al. |
| 2013/0296398 A1 | 11/2013 | Whalley et al. |
| 2013/0309306 A1 | 11/2013 | Rogawski et al. |
| 2014/0050789 A1 | 2/2014 | Bogawski et al. |
| 2014/0155456 A9 | 6/2014 | Whalley et al. |
| 2014/0243405 A1 | 8/2014 | Whalley et al. |
| 2014/0348926 A1 | 11/2014 | Hoffman et al. |
| 2015/0086494 A1 | 3/2015 | Sekura et al. |
| 2015/0265637 A1 | 9/2015 | Kane et al. |
| 2015/0359756 A1 | 12/2015 | Guy et al. |
| 2017/0027978 A1 | 2/2017 | Mukunda et al. |

FOREIGN PATENT DOCUMENTS

| | | |
|---|---|---|
| CA | 2424356 A | 4/2003 |
| WO | WO 2001/00196 A2 | 1/2001 |
| WO | WO 02/064109 A2 | 8/2002 |

(Continued)

OTHER PUBLICATIONS

Lowe (Potentiation of Ethanol-Induced Hepatic Vitamin A Depletion by Phenobarbital and Butylated Hydroxytoluene, Jan. 1987, Abstract Only).*
Okusada (Phase I and pharmacokinetic clinical trial of oral administration of the acyclic retinoid NIK-333, Apr. 2011, Abstract only).*
Consroe (Cannabidiol—Antiepileptic Drug Comparisons and interactions in experimentally induced seizures in Rats, Journal of Pharmacology and Experimental Therapeutics, 1976, vol. 201, No. 1, pp. 26-32).*
Phenobarbital (https://www.epilepsysociety.org.uk/phenobarbital#.XmaHcDbrufA, 2014).*
Jones (Cannabidiol exerts anti-convulsant effects in animal models of temporal lobe and partial seizures, Seizure 21 (2012) 344-352).*
Hosseinpour (Phenobarbital suppresses vitamin D3 25-hydroxylase expression: A potential new mechanism for drug-induced osteomalacia, Biochemical and Biophysical Research Communications 357 (2007) 603-607).*

(Continued)

*Primary Examiner* — Kathrien A Cruz
(74) *Attorney, Agent, or Firm* — Studebaker & Brackett PC

(57) ABSTRACT

The invention provides compositions and methods for treating seizure disorders such as epilepsy in humans and animals using, in a first embodiment, the combination of (i) an effective amount of a barbiturate drug, such as phenobarbital or primidone, which solely enhances GABAergic inhibition in a patient suffering a seizure disorder; and (ii) phytocannabinoid cannabidiol (CBD) in a dosage amount sufficient to overcome the hepatic metabolic effect stimulated by the barbiturate drug and provide bioavailable CBD to the patient in clinically efficacious amounts.

3 Claims, No Drawings

(56) References Cited

FOREIGN PATENT DOCUMENTS

| | | |
|---|---|---|
| WO | WO 2004/075896 A1 | 9/2004 |
| WO | WO 2010/048423 A1 | 4/2010 |
| WO | WO 2011/063164 A2 | 5/2011 |
| WO | WO 2011/110866 A1 | 9/2011 |
| WO | WO 2014/145490 A2 | 9/2014 |
| WO | WO 2016/044370 A1 | 3/2016 |
| WO | WO 2016/059399 A1 | 4/2016 |
| WO | WO 2016/118391 A1 | 7/2016 |
| WO | WO 2016/160542 A1 | 10/2016 |
| WO | WO 2017/027651 A1 | 2/2017 |
| WO | WO 2018/160510 A1 | 9/2018 |

OTHER PUBLICATIONS

Hollo (Correction of vitamin D deficiency improves seizure control in epilepsy: A pilot study, Epilepsy & Behavior 24 (2012) 131-133).*

U.S. Appl. No. 15/104,554, filed Jun. 15, 2016 (pending).

International Application S.N. PCT/US2017/037394, filed Jun. 14, 2017 (pending).

PCT Search Report dated Dec. 10, 2015, in International App. S.N. PCT/US2015/050342, filed Sep. 16, 2015 (9 pages).

PCT Search Report dated Mar. 16, 2016, in International App. S.N. PCT/US2016/013323, filed Jan. 14, 2016 (8 pages).

PCT Search Report dated Jun. 17, 2016, in International App. S.N. PCT/US2016/24145, filed Mar. 25, 2016 (10 pages).

PCT Search Report dated Oct. 31, 2016, in International App. S.N. PCT/US2016/46451, filed Aug. 11, 2016 (9 pages).

PCT Search Report dated Aug. 31, 2017, in International App. S.N. PCT/US2017/037394, filed Jun. 14, 2017 (10 pages).

Siemens et al., Effect of cannabis on pentobarbital-induced sleeping time and pentobarbital metabolism in the rat, Biochemical Pharmacology, vol. 23: 477-488, 1974 [retrieved on Feb. 25, 2016]. Retrieved from the internet : <URL: http://www.sciencedirect.com/science/article/pii/0006295274906121>abstract.

Schlanger, S et al., Diet Enriched with Omega-3 Fatty Acids Alleviates Convulsion Symptoms in Epilepsy Pateints. Epilepsia. 2002. vol. 43. No. 1; abstract; p. 103, first-second columns; p. 104, first column.

McMahan, K. Hemp Seed Oil—Why Should We Use It? Monterey Bay Hollistic Alliance. 2014; https://montereybayhollistic.wordpress.com/2014/08/23/hemp-seed-oil/; pp. 1-2, 4.

Kardinal. CG et al. Controlled trial of cyproheptadine in cancer patients with anorexia and/or cachexia. Cancer. Jun. 15, 1990. vol. 65. pp. 2657-2662; abstract; p. 2659. left column, 2nd, 4th paragraphs; p. 2661, right column, 2nd paragraph; table 5.

PCt Search Report dated Apr. 20, 2018 in International App. S.N. PCT/US2018/019814, filed Feb. 27, 2018 (11 pages).

* cited by examiner

COMPOSITION AND METHOD FOR TREATING SEIZURE DISORDERS

CROSS-REFERENCE TO RELATED APPLICATIONS

The present application claims priority on prior U.S. Provisional Application Ser. No. 62/107,432, filed Jan. 25, 2015, which is hereby incorporated herein in its entirety by reference.

FIELD OF THE INVENTION

This invention relates to compositions and methods for treating seizure disorders such as epilepsy in humans and animals (mammals) using phytocannabinoid cannabidiol (CBD) and a barbiturate drug which solely enhances GABAergic inhibition such as phenobarbital or primidone.

BACKGROUND OF THE INVENTION

Published Patent App. US 2013/0296398 reports that the combination of phytocannabinoid cannabidiol (CBD) with an anti-epileptic barbiturate drug, which solely enhances GABAergic inhibition, such as phenobarbital, appears not to provide any benefits in treating epilepsy when tested in a pilocarpine model.

Charalambous et al in BMC Veterinary Research 2014, 10:257 report on studies done to treat canine epilepsy using phenobarbital and other drugs, but baseline variations, study designs, and sources of bias preclude definitive recommendations.

SUMMARY OF THE INVENTION

The invention provides compositions and methods for treating seizure disorders such as epilepsy in humans and animals using, in a first embodiment, the combination of (i) an effective amount of a barbiturate drug, such as phenobarbital or primidone, which solely enhances GABAergic inhibition in a patient suffering a seizure disorder; and (ii) phytocannabinoid cannabidiol (CBD) in a dosage amount sufficient to overcome the hepatic metabolic effect stimulated by the barbiturate drug and provide bioavailable CBD to the patient in clinically efficacious amounts.

In a preferred embodiment, the drug combination includes a blocking compound, such as vitamin A, vitamin E, vitamin K, or the like compounds, in an amount effective to inhibit the hepatic metabolic effect of the barbiturate drug, thereby increasing the amount of bioavailable CBD to the patient.

Patients who are subject to seizure disorders such as epilepsy are treated to control and reduce the frequency of seizures by administering the drug combinations described above in accordance with further details of the invention that are disclosed herein.

DETAILED DESCRIPTION OF THE PREFERRED EMBODIMENT(S) OF THE INVENTION

In treating epilepsy, drugs such as phenobarbital or primidone, act by enhancing the GABAnergeric central nervous system inhibition. GABA is an acronym for gamma-aminobutyric acid and a GABAeric drug is a chemical which directly modulates the GABA system in the human body or brain. However, such compounds induce the cytochrome P450 hepatic system and the hepatic CYP2C19 enzyme chain that can metabolize phytocannabinoid cannabidiol (CBD). Thus any anti-seizure benefit expected from CBD is neutralized when combined with a barbiturate such as phenobarbital or primidone.

It has been found that these drawbacks can be overcome in two ways. First, by using a higher dose of CBD sufficient to inhibit and overcome the hepatic metabolic enhancement effect of a barbiturate and thus provide bioavailable CBD to a patient. And, secondly, by using a blocking compound in an amount effective to inhibit the hepatic metabolic effect of a barbiturate drug which in turn increases the amount of bioavailable CBD to the patient. It is believed that blocking compounds such as vitamins A, E or K degrade or metabolize enzymes produced or whose actions are enhanced by barbiturate drugs and thus at least partially prevent the degradation of CBD by such enzymes. The use of a blocking compound has the unexpected benefit of being able to use a lower dose of the barbiturate drug with CBD yet obtain the desired anti-convulsant effect expected from the use of barbiturate drug alone.

Chemically, phenobarbital is 5-ethyl-5-phenylpyrimidine-2,4,6(1H,3H,5H)-trione. It is a known, long-lasting barbiturate for treating epilepsy. Another barbiturate that can be used with the invention is primidone, chemically 5-ethyl-5-phenyl-hexahydropyrimidine-4,6-dione. Primidone is available under the brandname Mysoline.

CBD can be used in its pure form or as a mixture of compounds that result from extracting *cannabis* plants. Such mixtures contain CBD, THC or tetrahydrocannabinol (which in turn is a mixture comprising 9-tetrahydrocannabinol (delta-9 THC), 8-tetrahydrocannabinol (delta-8 THC) and 9-THC Acid), Cannabinol (CBN), Cannabichromene (CBC), Cannabigerol (CBG), terpenoids and flavonoids.

The preferred CBD mixture is extracted from a *Cannabis Indica*, the composition of which is known. The use of CBD from *Cannabis Indica*, which can contain up to 50% THC (based on the amount of CBD), is preferred. See, for example, Qureshi et al, World Applied Sciences Journal 19 (7): 918-923, 2012 ISSN 1818-4952, IDOSI Publications, 2012, disclosing an Indicia extraction containing 54% CBD and 24% THC. Preferred mixtures for use in the invention contain at least 50% by weight CBD wherein the weight ratio of CBD to THC is at least 2:1, preferably at least 3:1.

The preferred CBD mixture is extracted from a *Cannabis Indica* dominant strain using high pressure and carbon dioxide as a solvent in a 1500-20L subcritical/supercritical $CO_2$ system made by Apeks Super Critical Systems, 14381 Blamer Rd., Johnstown, Ohio, 43031. See http://www.apekssupercritical.com/botanical-extraction-systems/

Apeks Systems use valveless expansion technology with no constrictions or regulating valves to cause clogging in the system between the extraction vessel and the $CO_2$ expansion separator. Flow of liquid $CO_2$ and dissolved oil travels from the extraction vessel into the separator, and the oil is separated from the $CO_2$ in the separator/collection vessel. $CO_2$ is recycled during the extraction process and recovered and regenerative heat capture methods are used to increase efficiency.

A further process using solvents can be used to remove THC from the mixture leaving either pure CBD or so-called "Organic CBD" containing CBD, CBN, CBC, CBG CBN, terpenoids and flavonoids. The use of essentially THC-free Organic CBD from *Cannabis Indica* is more preferred.

Another source of CBD essentially free of THC is the CBD mixture obtained by extracting hempseed oil. See Leizer et al, J. Nutraceuticals, Functional and Medical Foods, Vol. 2(4) 2000, The Haworth Press, Inc. Elixinol (D&G Health LLC) is a predominantly CBD product extracted from hempseed oil that contains trace amounts of THC.

The preferred blocking compound is vitamin A which is a group of unsaturated compounds that includes retinol, retinal, retinoid acid, beta-carotene and other provitamin A carotenoids.

Other useful blocking compounds that inhibit the hepatic metabolic effect of barbiturates include vitamins D, E and K. Vitamin A is preferred because it is less likely to interact with other medications.

Vitamin E is commonly gamma-tocopherol from corn or soybean oil, or alpha-tocopherol from wheat germ oil or sunflower and safflower oils. Vitamin K is synthesized by plants and is a family 2-methyl-1,4-naphthoquinone (3-) derivatives.

Patients being treated for seizure disorders will receive a barbiturate drug, phenobarbital or primidone, in an amount to provide from about 15 to about 40 micrograms of the drug per milliliter of blood serum in a patient. To obtain these levels, the dosage amount of the barbiturate drug will be not greater that about 2 mg/kg of patient weight.

The dosage amount of CBD to be used with phenobarbital or primidone is from about 0.5 to about 1.0 mg/kg of patient weight. When used with phenobarbital or primidone and CBD, the dosage amount of a blocking compound such as vitamin A will be not less than about 0.5 mg/kg of patient weight.

Candidates to be treated according to the invention will generally present with symptoms or signs associated with seizure disorders such as recurrent loss of consciousness, recurrent seizures and/or a prior diagnoses of medically refractory epilepsy. The invention is especially useful in treating patients who have had recurrent and/or poorly controlled seizures or epilepsy in spite of being treated with one or more know anticonvulsant drugs.

The expected response in patients treated according to the invention is a reduction in seizure intensity and/or frequency once a steady state of the active pharmaceutical components is achieved. Up to 14 or more days of treatment may be required before benefits can be achieved.

Patients with allergies, cardiac rhythm disturbances, metabolic syndrome or a history of *Cannabis* abuse are not candidates to be treated according to the invention.

Animals, especially dogs and cats, can be treated according to the invention. Seizures in dogs and cats are caused by abnormal brain activity; they can to subtle or cause violent convulsions. Some seizures only occur once but repeated seizures require treatment to prevent larger areas of the brain from becoming affected. Dosage amounts and serum levels of drug are the same as disclosed above for human patients.

While this invention has been described as having preferred sequences, ranges, ratios, steps, order of steps, materials, structures, symbols, indicia, graphics, color scheme(s), shapes, configurations, features, components, or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the claims appended hereto or presented later. The invention, therefore, is not limited to the preferred embodiment(s) shown/described herein.

What is claimed is:

1. A method for treating epilepsy consisting essentially of administering to a patient in need thereof a composition comprising as sole pharmaceutical components: (i) a barbiturate drug selected from the group consisting of phenobarbital and primidone in an amount not greater than 2 mg/kg of patient weight, (ii) phytocannabinoid cannabidiol (CBD) in a dosage amount of from 0.5 to 1.0 mg/kg of patient weight; and (iii) a blocking compound selected from the group consisting of vitamins A, D, E and K in an amount of less than 0.5 mg/kg of patient weight, which is effective to inhibit the hepatic metabolic effect of phenobarbital or primidone, thereby increasing the amount of bioavailable CBD to said patient.

2. Method of claim 1 wherein the CBD is extracted from *Cannabis indica* or hempseed oil.

3. Method of claim 1 wherein the CBD is essentially free of tetrahydrocannabinol (THC).

* * * * *